(12) United States Patent
Yang

(10) Patent No.: US 7,553,497 B2
(45) Date of Patent: Jun. 30, 2009

(54) GELATIN HARD CAPSULE ENHANCING THE FILM STRENGTH

(75) Inventor: Joo Hwan Yang, Kyonggi-do (KR)

(73) Assignee: Suheung Capsule Co., Ltd., Kyonggi-do (KR)

( * ) Notice: Subject to any disclaimer, the term of this patent is extended or adjusted under 35 U.S.C. 154(b) by 671 days.

(21) Appl. No.: 11/088,779

(22) Filed: Mar. 25, 2005

(65) Prior Publication Data

US 2006/0188567 A1    Aug. 24, 2006

(30) Foreign Application Priority Data

Feb. 21, 2005    (KR) .................. 10-2005-0014138

(51) Int. Cl.
*A61K 9/48* (2006.01)
*A61K 9/64* (2006.01)

(52) U.S. Cl. ...................... 424/451; 424/456

(58) Field of Classification Search ................. 424/451, 424/456
See application file for complete search history.

(56) References Cited

U.S. PATENT DOCUMENTS 5,419,916 A * 5/1995 Yamamoto et al. .......... 424/456
6,740,333 B2 * 5/2004 Beckett et al. ............... 424/436

FOREIGN PATENT DOCUMENTS

EP    1210936 A1 *    6/2002
JP    2001170137    *    6/2001

* cited by examiner

*Primary Examiner*—Raymond J Henley, III
(74) *Attorney, Agent, or Firm*—Jacobson Holman PLLC

(57) ABSTRACT

A process for preparing gelatin hard capsule having enhanced film strength by the steps including i) adding 1~10 wt part of PEG mixture of PEG 600 and PEG 1500 in weight ratio 40~60:60~40 to the solution having 100 wt part of gelatin; ii) adding 0.1~1.2 wt part of emulsifier mixture containing acetyl glycerine fatty acid ester and sodium lauryl sulfate to the resulting mixture; and iii) allowing the obtained mixture to stand, adjusting its viscosity and forming a hard capsule therefrom. Further, this gelatin hard capsule has equal film distribution with minimum cracking or chipping when hygroscopic material is inserted.

2 Claims, No Drawings

GELATIN HARD CAPSULE ENHANCING THE FILM STRENGTH

BACKGROUND OF THE INVENTION

The present invention relates to a gelatin hard capsule enhancing the strength of film. More particularly, this invention relates to a gelatine hard capsule having enhanced strength of film and equal film distribution prepared by the steps comprising i) adding polyethylene glycol (PEG) and acetyl glycerine fatty acid ester to gelatin aqueous solution; and ii) forming and drying the gelatin mixture.

In particular, this invention concerns gelatin hard capsule having minimum cracking or chipping in low moisture condition prepared by the steps comprising i) selecting PEG among PEGs having average M.W. 200~20,000; ii) preparing proper PEG mixture using selected PEGs; iii) adding said PEG mixture with acetyl glycerine fatty acid ester as plasticizer to gelatin aqueous solution; and iv) forming and drying the gelatine mixture to obtain gelatin hard capsule.

Gelatin reversibly changes its phase from sol into gel according to the change of temperature. The water content of gelatin film is 13~16% and gelatine capsules are widely used in the field of pharmaceutical or food stuff preparation. However, conventional hard gelatin capsules have a problem in that the capsule film loses flexibility and suffers cracking or chipping if the capsules are packed with a hygroscopic drug such as a powder or granular material since the moisture contained in the capsule film is adsorbed by the drug.

To solve above problems, addition of PEG to gelatin film composition has been suggested.

Japanese laying open patent publication No. 3-80930 'Composition of gelatin film' disclosed the gelatin film composition comprising polyethylene glycol of average M.W. 200~20,000. Among them, at least one PEG selected from the group consisting of 200, 300, 400, 600, 1000, 1500, 1540, 4000, 6000 and 20000 has been disclosed. However, there is no description which M.W. of PEG is selectively proper for protecting the decline of water content in gelatine capsule.

In Japanese Pat. No. 3,320,802, gelatine hard capsule film composition comprising 1~10 wt % of polyvinylacetyldiethylaminoacetate and 1~10 wt % of PEG as to gelatin has been disclosed. This gelatin film composition can be used for protecting the decline of water content of gelatin film when hygroscopic drug is contained. Further, this gelatin film composition affords the minimum cracking or chipping, which prevents the leakage of drug.

In Japanese Pharmacopoeia, 5 kinds of PEGs, according to the size of M.W., 400, 1500, 4000, 6000, 20000 are described. In the Japanese specification of drug additive, 5 kinds of PEGs 200, 300, 600, 1000, 1540 are described. However, in Japanese Pat. No. 3,320,802, it has not been specifically disclosed which PEG among them is desirously used, except that PEG 4000 is proper in this disclosure.

On the other hand, Japanese Pat. No. 3,594,111 discloses a preparation method for hard capsule according to the dipping method by addition of PEG 1540 to gelatin aqueous solution. In this disclosure, the method comprises i) adding 10~50 wt % of PEG 1540 as to gelatin content in gelatin aqueous solution; and ii) forming gelatin hard capsule according to dipping method. The PEG added to gelatin is only PEG 1540 in this disclosure.

Gelatin hard capsule has been manufactured using the characteristics of gelatin having setting point at 25~28° C. To obtain a flat film minimizing the cracking or chipping with equal film distribution, it is required that the setting point of PEG added to gelatin solution shall be same or similar to that of gelatin, which enables the flow of gelatin mixed solution to be constant at the mold pin after dipping.

Because 10 kinds of PEGs described in Japanese Pharmacopoeia and Japanese specification of drug additive have different physical properties such as setting point and viscosity, the selection of proper PEG has been required to achieve the gelatin hard capsule having equal film distribution and minimum cracking or chipping.

However, it has not been disclosed yet which grade of PEG is compatible to gelatin base to accomplish the enhancement of film strength and protection of decline of water content when hygroscopic material is inserted.

The inventors have developed a gelatin hard capsule by adding proper PEG mixture to gelatin, which enhances the film strength when hygroscopic material is inserted. Further, this gelatin hard capsule has equal film distribution with minimum cracking or chipping when hygroscopic material is inserted.

SUMMARY OF THE INVENTION

The object of the present invention is to provide a process for preparing gelatin hard capsule having enhanced film strength by the steps comprising;

i) adding 1~10 wt part of PEG mixture of PEG 600 and PEG 1500 in weight ratio 40~60:60~40 to the solution having 100 wt part of gelatin;

ii) adding 0.1~1.2 wt part of emulsifier mixture containing acetyl glycerine fatty acid ester and sodium lauryl sulfate to the resulting mixture; and iii) allowing the obtained mixture to stand, adjusting its viscosity and forming a hard capsule therefrom.

Further, the weight ratio of PEG 600 and PEG 1500 is preferably 50:50 and the content of said PEG mixture is preferably 4~8 wt part.

Also, the content of acetyl glycerine fatty acid ester is 0.1~1 wt part and the content of sodium lauryl sulfate is 0.05~0.2 wt part.

On the other hand, the present invention also provides a gelatin hard capsule prepared by above preparation method comprising 100 wt part of gelatin, 1~10 wt part of PEG mixture, 0.1~1 wt part of acetyl glycerine fatty acid ester and 0.05~0.2 wt part of sodium lauryl sulfate.

DETAILED DESCRIPTION OF THE INVENTION

For selecting the proper PEG to be added to the gelatin solution, the physical properties of PEG according to M.W. have been researched. The setting point and viscosity of PEG has been disclosed in Handbook of Pharmaceutical Excipients. Table 1 shows the data of setting point and viscosity of PEGs.

TABLE 1

The data of setting point and viscosity of PEGs.

| Item | | Grade of PEG | | | | | | | | |
|---|---|---|---|---|---|---|---|---|---|---|
| | | 200 | 300 | 400 | 600 | 1000 | 1500 | 1540 | 4000 | 6000 | 20000 |
| Setting point ° C. | | — | — | 4-8 | 18-23 | 35-40 | 37-41 | 43-47 | 53-57 | 56-61 | 56-64 |
| Viscosity (mm²/s) | 25° C. | 39.9 | 68.8 | 90 | 131 | Soild | Soild | Soild | Soild | Soild | Soild |
| | 99° C. | 4.4 | 5.9 | 7.4 | 11.0 | 19.5 | 15.0 | 47 | 180 | 580 | 6900 |

As shown in Table 1, the setting point and viscosity of PEG increase according to the increase of PEG M.W. Since PEG 4000, 6000, 20000 have setting point at more than 53° C., it is required that dipping temperature of gelatin mixture has to be more than 53° C. for mixing these PEGs with gelatin. Considering the fact that ordinary dipping temperature is less than 50° C., these PEGs cannot be used due to the incompatibility with gelatin for producing gelatin capsule.

On the other hand, PEG 200, 300, 400 also cannot be used for improving the film strength, due to their high hygroscopic properties, which causes the high flexibility of capsule and delay of drying film.

Therefore, considering the physical properties of setting point and viscosity of PEGs, the proper PEGs for improving the film strength shall be PEG 600 and PEG 1500. The preferred PEG may be the mixture of these PEGs.

If only setting point is considered, PEG 600 is preferred due to similar setting point of gelatin. However, only addition of PEG 600 cannot solve the problem of cracking or chipping because PEG 600 has some hygroscopic property. On the other hand, PEG 1500 has an advantage for preparing film due to its relative low viscosity compared to that of PEG 1000. However, only addition of PEG 1500 may result in the uneven of film distribution because relative high setting point hinders the flow of gelatin solution during the preparation procedure.

Therefore, it is concluded that the mixture of PEG 600 and PEG 1500 in a proper ratio will be a proper PEG for enhancing film strength, which solves the problems raised by the addition of each PEG only. Preferred weight ratio of PEG 600 and PEG 1500 is 50:50. Further, to enhance the mechanical strength of gelatin film, acetyl glycerine fatty acid ester can be added as plasticizer. Acetyl glycerine fatty acid ester also has a function for enhancing flexibility and sliding of gelatin film.

The properties of PEG and emulsifier used in present invention can be explained as follows.

PEG 1500 has a paste form in room temperature. PEG 600 has a sticky liquid form at more than 20° C. and has a paste form less than 20° C. Acetyl glycerine fatty acid ester has a clear liquid form in oily phase.

Further, the weight ratio of PEG 600 and PEG 1500 is preferably 50:50 and the content of said PEG mixture is preferably 4~8 wt part. If the content of PEG mixture is less than 4 wt part, the property for protecting cracking or chipping the capsule cannot be satisfactory. If the content of PEG mixture is more than 8 wt part, the film distribution of capsule cannot be satisfactory. Further, the content of acetyl glycerine fatty acid ester is preferably 0.3~0.8 wt part, while the content of sodium lauryl sulfate is preferably 0.05~0.2 wt part.

The preparation method for gelatin hard capsule of present invention can be explained as follows.

After weighing and mixing the PEG 600 and PEG 1500 in 50:50 wt ratio, this mixture is dissolved with purified water (Mixed solution A). Purified water, sodium lauryl sulfate and acetyl glycerine fatty acid ester are mixed for homogenization (Mixed solution B). Mixed solution A and Mixed solution B are added subsequently to the gelatin aqueous solution. Then, the mixture is stirred and a small amount of titanium oxide and coloring agent is added. Finally, the mixture stands for adjusting viscosity, and aging and forming the capsule.

The present invention will be more specifically explained by the following examples. However, it should be understood that the examples are intended to illustrate but not in any manner to limit the scope of the present invention.

EXAMPLE 1

Preparation of Gelatin Hard Capsule of Present Invention 12.5 kg of PEG 600 (concentration: 25%) and 12.5 kg of PEG 1500 (concentration: 25%) are added and stirred until completely dissolved to 25 L of purified water at 60° C. Then, mixed solution is prepared (Mixed solution A). In the other bowl, 12.5 L of purified water is added at 60° C. Then, 0.5 kg of sodium lauryl sulfate (concentration: 3.3%) is added and homogenized in high speed stirrer at 3000 rpm and 2.0 kg of acetyl glycerine fatty acid ester (concentration: 13.3%) is added and homogenized in high speed stirrer for 2 hours. Then, mixed solution is prepared (Mixed solution B). 5 wt part of Mixed solution A is added to gelatin aqueous solution (concentration: 32%) as to 100 wt part of gelatin content. Subsequently, 0.4 wt part of Mixed solution B is added to gelatin aqueous solution (concentration: 32%) as to 100 wt part of gelatin content. After stirring said mixture in 60 rpm for 2 hours, Mixed solution A and B with gelatin solution are homogenized. Then, 1.5 wt part of titanium oxide is added. After adjusting viscosity, the mixture is aged for 4 hours with sealing. Resulting mixed solution is input to capsule manufacturing machine to prepare Size 2 white capsule.

COMPARATIVE EXAMPLE 1

Preparation of Gelatin Hard Capsule for Control Group

Gelatin hard capsule is prepared as the same manner of Example 1 except that only Mixed solution A is added instead of Mixed solution A and B. However, 0.1 wt part of sodium lauryl sulfate is added for preparation of capsule.

COMPARATIVE EXAMPLE 2

Preparation of Gelatin Hard Capsule for Control Group

Gelatin hard capsule is prepared as the same manner of Comparative Example 1 except that only PEG 600 is added instead of Mixed solution A.

COMPARATIVE EXAMPLE 3

Preparation of Gelatin Hard Capsule for Control Group

Gelatin hard capsule is prepared as the same manner of Comparative Example 1 except that only PEG 1500 is added instead of Mixed solution A.

COMPARATIVE EXAMPLE 4

Preparation of Commercially Marketed Gelatin Hard Capsule

Commercially marketed gelatin hard capsule Size 2 is prepared containing 1.5 wt part of titanium oxide.

EXAMPLE 2

Impact Test of Empty Capsule

The capsules prepared in Example 1 and Comparative Examples 1~4 have been stored in dry-oven at 50° C. to control the water content of capsule. Said capsules are laid on Impact Tester (made by inventor) to examine the cracking rate when 50 g of hammer is dropped from 10 cm of height. The cracking status of capsule is detected by visual examination. Table 2 shows the results of cracking of capsules.

TABLE 2

The results of cracking of capsules

| | | Cracking ratio (%), n = 50 | | |
|---|---|---|---|---|
| Item | Composition | Water Content of gelatin capsule 7.5% | Water Content of gelatin capsule 6.5% | Water Content of gelatin capsule 5.5% |
| Examp. 1 | PEG 600 + PEG 1500 + acetyl glycerine fatty acid ester | 8 | 31 | 53 |
| Comp. Examp. 1 | PEG 600 + PEG 1500 | 24 | 42 | 76 |
| Comp. Examp. 2 | PEG 600 | 32 | 50 | 84 |
| Comp. Examp. 3 | PEG 1500 | 32 | 46 | 86 |
| Comp. Examp. 4 | Commercially marketed capsule | 55 | 72 | 98 |

As shown in Table 2, adding the mixture of PEG 600 and PEG 1500 enhances the film strength of gelatin capsule to prevent cracking (Comparative Example 1). Further, additional adding the acetyl glycerine fatty acid ester to PEG mixture far enhances the film strength of gelatin capsule (Example 1). Therefore, the gelatin hard capsule according to present invention shows excellent prevention of cracking compared to commercially marketed capsule or only PEG adding capsule.

EXAMPLE 3

Film Distribution Test

The capsules prepared in Example 1 and Comparative Examples 1~4 have been used for test materials of film distribution test. The results of film distribution are shown in Table 3.

TABLE 3

The results of film distribution

| | | Thickness of capsule film (mm), n = 20 | | | |
|---|---|---|---|---|---|
| Item | | Average | Maximum | Minimum | Range |
| Examp. 1 | cap | 0.096 | 0.100 | 0.091 | 0.010 |
| | body | 0.095 | 0.099 | 0.090 | 0.009 |
| Comp. Examp. 1 | cap | 0.097 | 0.101 | 0.091 | 0.010 |
| | body | 0.096 | 0.100 | 0.090 | 0.010 |
| Comp. Examp. 2 | cap | 0.103 | 0.111 | 0.095 | 0.016 |
| | body | 0.102 | 0.109 | 0.094 | 0.015 |
| Comp. Examp. 3 | cap | 0.086 | 0.097 | 0.075 | 0.022 |
| | body | 0.084 | 0.095 | 0.073 | 0.022 |
| Comp. Examp. 4 | cap | 0.097 | 0.101 | 0.092 | 0.009 |
| | body | 0.096 | 0.100 | 0.091 | 0.009 |

As shown in Table 3, adding PEG 600 only causes the thick film distribution of capsule at cutting line by delaying the hardening of gelatin solution in molding pin as well as by laying down of gelatin solution. Further, standard deviation of thickness of film is also high (Comparative Example 2). Further, adding PEG 1500 only causes the thin film distribution of capsule by fastening the hardening of gelatin solution in molding pin as well as by inhibiting the flow of gelatin solution. Further, standard deviation of thickness of film is also high (Comparative Example 3). However, mixture of PEG 600 and PEG 1500 solves the problem of film distribution. Therefore, the film distribution of the capsule in Example 1 enables the similar or same film distribution compared to that of commercially marketed product.

This invention can afford a gelatin hard capsule by adding proper PEG mixture to gelatin, which enhances the film strength when hygroscopic material is inserted. Further, this gelatin hard capsule of present invention has equal film distribution with minimum cracking or chipping when hygroscopic material is inserted.

What is claimed is:

1. A process for preparing gelatin hard capsule having enhanced film strength by the steps comprising;
    i) adding 4~8 wt part of PEG mixture of PEG 600 and PEG 1500 in weight ratio 40~60:60~40 to the solution having 100 wt part of gelatin;
    ii) adding 0.1~1.2 wt part of emulsifier mixture containing 0.1~1.0 wt part of acetyl glycerine fatty acid ester and 0.05~0.2 wt part of sodium lauryl sulfate to the resulting mixture; and
    iii) allowing the obtained mixture to stand, adjusting its viscosity and forming a hard capsule therefrom.

2. The process for preparing gelatin hard capsule according to claim 1, wherein the weight ratio of PEG 600 and PEG 1500 is 50:50.

* * * * *